(12) United States Patent
Wang

(10) Patent No.: US 12,193,326 B2
(45) Date of Patent: Jan. 7, 2025

(54) ELECTRON TRANSPORT MATERIAL AND FABRICATING METHOD THEREOF, AND ORGANIC LIGHT-EMITTING DIODE

(71) Applicants: Wuhan China Star Optoelectronics Technology Co., Ltd., Hubei (CN); Wuhan China Star Optoelectronics Semiconductor Display Technology Co., Ltd., Hubei (CN)

(72) Inventor: Kui Wang, Hubei (CN)

(73) Assignees: Wuhan China Star Optoelectronics Technology Co., Ltd., Wuhan (CN); Wuhan China Star Optoelectronics Semiconductor Display Technology Co., Ltd., Wuhan (CN)

( * ) Notice: Subject to any disclaimer, the term of this patent is extended or adjusted under 35 U.S.C. 154(b) by 0 days.

(21) Appl. No.: 17/424,906

(22) PCT Filed: Jun. 3, 2021

(86) PCT No.: PCT/CN2021/098125
§ 371 (c)(1),
(2) Date: Jul. 22, 2021

(87) PCT Pub. No.: WO2022/241854
PCT Pub. Date: Nov. 24, 2022

(65) Prior Publication Data
US 2024/0032419 A1    Jan. 25, 2024

(30) Foreign Application Priority Data
May 20, 2021    (CN) .......................... 202110554957.0

(51) Int. Cl.
*H10K 85/60*     (2023.01)
*C07D 471/22*    (2006.01)
*H10K 50/16*     (2023.01)

(52) U.S. Cl.
CPC ....... *H10K 85/6572* (2023.02); *C07D 471/22* (2013.01); *H10K 85/626* (2023.02); *H10K 50/16* (2023.02)

(58) Field of Classification Search
CPC .. H10K 85/6572; H10K 85/626; H10K 50/16; C07D 471/02; C07D 405/04; C07D 405/10; C07D 405/14; C07D 409/04; C07D 409/10; C07D 409/14; C07D 471/14; H01L 51/0072; H01L 51/0067; H01L 51/0073; H01L 51/0074; H01L 51/5016; H01L 51/5036; C07F 9/587; C07F 15/06; C09K 2211/1029; C09K 2211/1044; C09K 2211/18
See application file for complete search history.

(56) References Cited

U.S. PATENT DOCUMENTS

2009/0136779 A1    5/2009   Cheng et al.

FOREIGN PATENT DOCUMENTS

| CN | 101001935 | 7/2007 |
|---|---|---|
| CN | 108276336 | 7/2018 |
| CN | 110627834 | 12/2019 |
| CN | 111018783 | 4/2020 |

*Primary Examiner* — Shane Fang

(57) ABSTRACT

An electron transport material and a fabricating method thereof according to embodiments of the present application are described, which relate to displays. The electron transport material has high electron mobility, which can improve a luminous efficiency of an OLED device. The fabricating method is simple to operate, and a performance of the organic light-emitting diode fabricating by using the electron transport material is also good.

20 Claims, No Drawings

ELECTRON TRANSPORT MATERIAL AND FABRICATING METHOD THEREOF, AND ORGANIC LIGHT-EMITTING DIODE

RELATED APPLICATIONS

This application is a National Phase of PCT Patent Application No. PCT/CN2021/098125 having International filing date of Jun. 3, 2021, which claims the benefit of priority of Chinese Patent Application No. 202110554957.0 filed on May 20, 2021. The contents of the above applications are all incorporated by reference as if fully set forth herein in their entirety.

FIELD AND BACKGROUND OF THE INVENTION

The present disclosure relates to displays, and more particularly to an electron transport material and a fabricating method thereof, and an organic light-emitting diode.

In an organic light-emitting diode (OLED), electron transport materials have functions of balancing carriers, enhancing electron injection, reducing operating voltage, and achieving exciton blocking. A general selection criteria includes:

(1) a higher electron mobility: a carrier balance of organic light-emitting diodes has a significant impact on its efficiency and stability, and the electron mobility of existing hole transport materials is 1 to 2 orders of magnitude higher than that of electron transport materials. Therefore, improving the electron mobility of the electron transport material is beneficial to the carrier balance, which can improve an efficiency of a device;

(2) a suitable energy level: the deeper LUMO (lowest unoccupied molecular orbital) energy level is conducive to an injection of electrons from a cathode to reduce a turn-on voltage. The deeper HOMO (highest occupied molecular orbital) energy level can play a role in confining the holes injected from the anode to the light-emitting layer, thereby improving an efficiency of carrier recombination;

(3) a higher triplet energy level: due to a longer lifetime of triplet excitons, a range of their diffusion is larger. The electron transport material with a higher triplet energy level can effectively block the triplet excitons generated by the recombination of carriers in the light-emitting layer. Therefore, they cannot diffuse to the electron transport layer, thereby improving an efficiency of the device; and (4) good thermal stability and film-forming properties: it is beneficial to help to improve the stability of the device.

The electron transport material used in traditional organic light-emitting diodes is 8-Hydroxyquinoline aluminum salt (Alq3), but the electron mobility of 8-Hydroxyquinoline aluminum salt is relatively low ($10^{-6}$ cm$^2$/Vs). Therefore, the electron transport and hole transport of the device are not balanced. With a commercialization and practicality of organic light-emitting diodes, people hope to obtain electronic transport materials with higher transmission efficiency and better practical performance.

Currently, more electron transport materials are used, such as bathophenanthroline (BPhen), bathocuproine (BCP) and TmPyPB, which can generally meet a market demand for organic electroluminescent panels. However, a glass transition temperature of these materials is relatively low (generally less than 85° C.). When the device is running, a Joule heat generated will cause molecular degradation and changes in molecular structure, resulting in reduced panel efficiency and poor thermal stability. In addition, a molecular structure of these materials is regular and symmetrical, and crystallization is prone to occur after a long time. Once the electron transport material crystallizes, the charge transition mechanism between molecules will be different from the charge transition mechanism in the normal operating amorphous film state, resulting in a decrease in the electron transport performance. As a result, the electron and hole mobility of the entire device is unbalanced, the exciton formation efficiency is significantly reduced, and the exciton formation is concentrated at the interface between the electron transport layer and the light-emitting layer, resulting in a serious decrease in device efficiency and lifetime. Therefore, there is an urgent need for an electron transport material with excellent performance to solve above problems.

SUMMARY OF THE INVENTION

Embodiments of the present application provide an electron transport material, which has a high electron mobility and can improve a luminous efficiency of an OLED device. Embodiments of the present application also provide a fabricating method of the electron transport material and an applied organic light-emitting diode. The fabricating method is simple to operate and the applied organic light-emitting diode has good performance.

An embodiment of the present application provides an electron transport material, wherein a molecular structure of the electron transport material has a structural formula shown in formula (I):

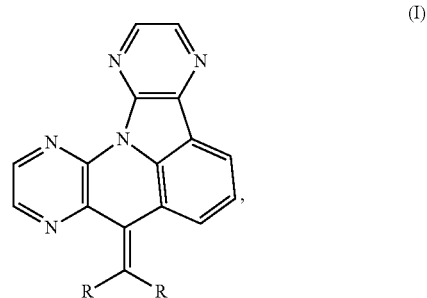

wherein, each time R appears, each R is independently selected from one or more of a C6-C60 substituted aryl group, a C6-C60 unsubstituted aryl group, or a C3-C60 heteroaryl group.

Optionally, in some embodiments of the present application, the unsubstituted aryl group comprises:

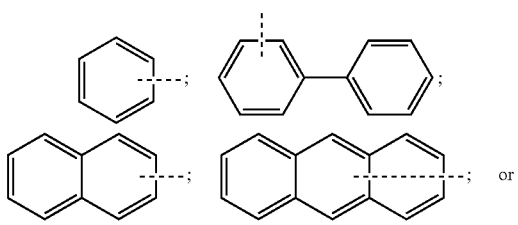

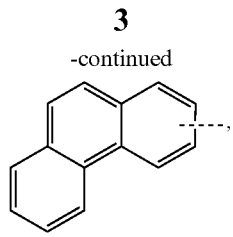

wherein a dotted line indicates a connection site.

Optionally, in some embodiments of the present application, the substituted aryl group comprises:

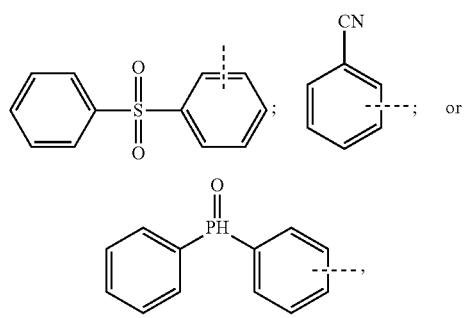

wherein a dotted line indicates a connection site.

Optionally, in some embodiments of the present application, the heteroaryl group comprises:

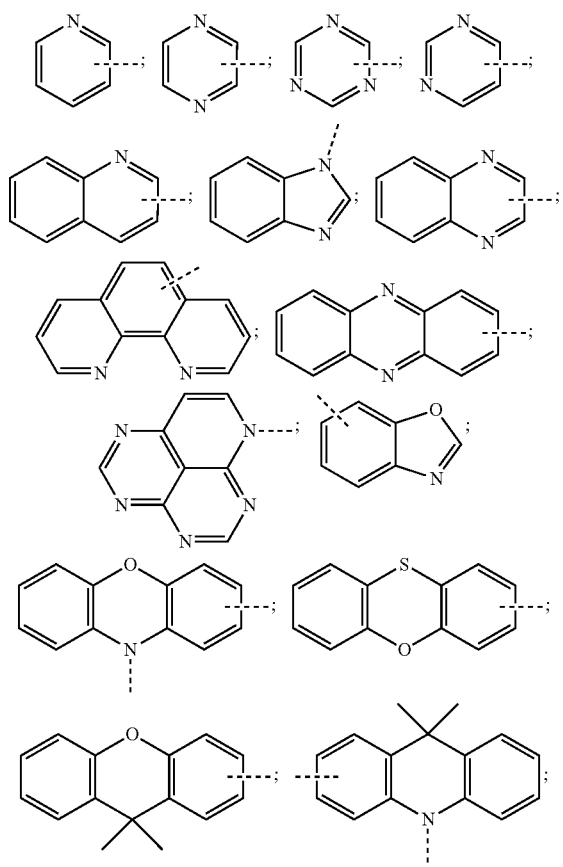

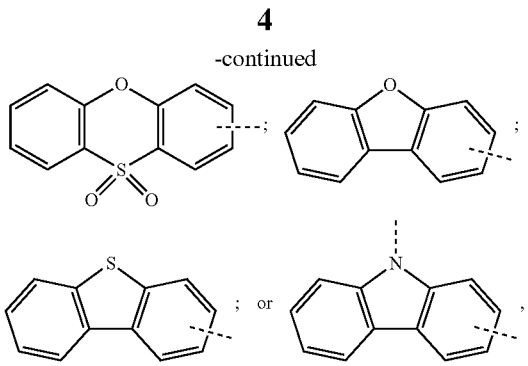

wherein a dotted line indicates a connection site.

Correspondingly, an embodiment of the present application also provides a method of fabricating an electron transport material, which includes following steps:

fabricating the electron transport material based on a McMurray reaction of a first compound and a second compound, wherein: a structural formula of the first compound is as formula (II):

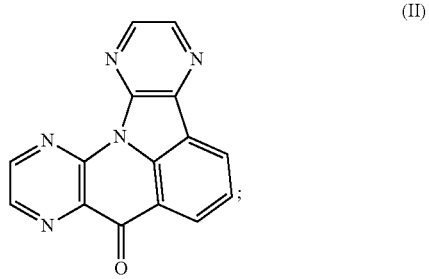 [SMILES: O=c1c2cccc3c4nccnc4n(c4nccnc14)c23]

and
a structural formula of the second compound is as formula (III):

wherein, each time R1 appears, each R1 is independently selected from one or more of a C6-C60 substituted aryl group, a C6-C60 unsubstituted aryl group, or a C3-C60 heteroaryl group.

Optionally, in some embodiments of the present application, a molar ratio of the first compound to the second compound is 0.8~1.2:0.8~1.2.

Optionally, in some embodiments of the present application, the second compound is selected from one or more of:

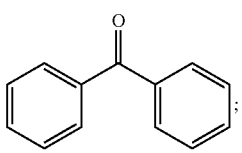

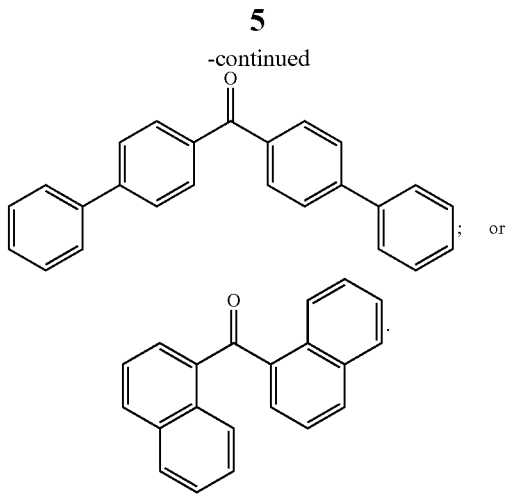
; or

Optionally, in some embodiments of the present application, the step of fabricating the electron transport material based on the McMurray reaction of the first compound and the second compound comprises steps of:
providing a reaction solvent and a catalyst for the McMurray reaction; and
reacting the first compound and the second compound under conditions of the reaction solvent and the catalyst until conversion rates of the first compound and the second compound are both above 95%; and
extracting an organic matter after quenching.

Optionally, in some embodiments of the present application, the step of reacting the first compound and the second compound under conditions of the reaction solvent and the catalyst comprises steps of:
mixing and reacting the reaction solvent with the catalyst to obtain a mixture; and
mixing the organic solvent with the mixture and heating to reflux, wherein the first compound and the second compound are dissolved in the organic solvent.

Optionally, in some embodiments of the present application, a molar ratio of the first compound to the organic solvent is 0.8~1.2:9~10.

Optionally, in some embodiments of the present application, the step of quenching comprises: quenching with a carbonate solution after a substance obtained by the reaction is cooled to room temperature.

Optionally, in some embodiments of the present application, the step of quenching comprises: a mass concentration of the carbonate solution is 8-12%.

Optionally, in some embodiments of the present application, the catalyst comprises a first catalyst and a second catalyst, and a molar ratio of the reaction solvent, the first catalyst, and the second catalyst is 35-45:1.5-2.5:0.8-1.2.

Optionally, in some embodiments of the present application, the first catalyst is metal powder, and the second catalyst is titanium chloride.

Optionally, in some embodiments of the present application, the conversion rates of the first compound and the second compound are monitored by high performance liquid chromatography.

Further, an embodiment of the present application further provides an organic light-emitting diode, comprising an electron transport layer. The electron transport layer comprises an electron transport material, and a molecular structure of the electron transport material has a structural formula shown in formula (I):

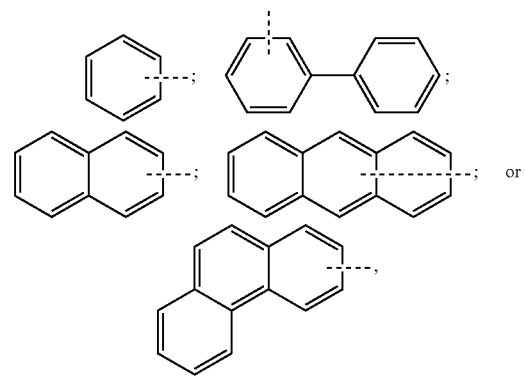

wherein, each time R appears, each R is independently selected from one or more of a C6-C60 substituted aryl group, a C6-C60 unsubstituted aryl group, or a C3-C60 heteroaryl group.

Optionally, in some embodiments of the present application, the unsubstituted aryl group comprises:

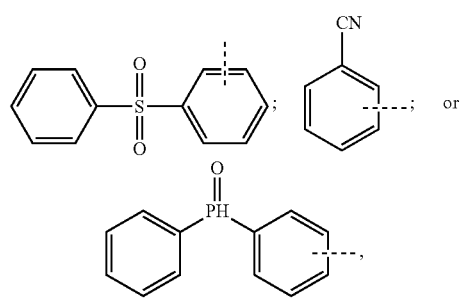

wherein a dotted line indicates a connection site.

Optionally, in some embodiments of the present application, the substituted aryl group comprises:

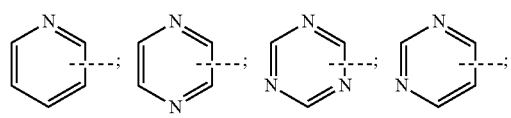

wherein a dotted line indicates a connection site.

Optionally, in some embodiments of the present application, the heteroaryl group comprises:

-continued

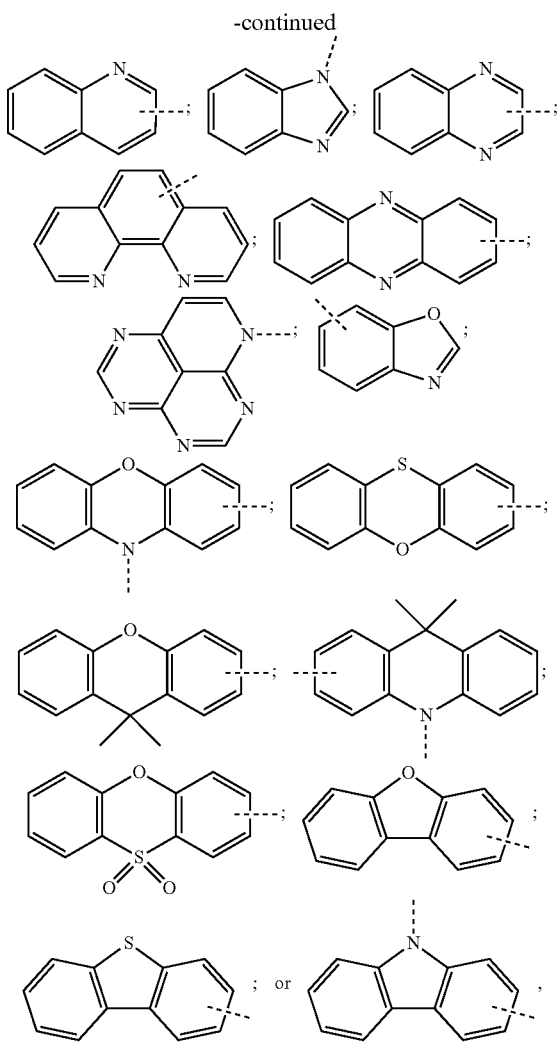

wherein a dotted line indicates a connection site.

Optionally, in some embodiments of the present application, the organic light-emitting diode further comprises: a cathode, a light-emitting layer, a hole transport layer, and an anode, wherein the anode, the hole transport layer, the light-emitting layer, the electron transport layer, and the cathode are laminated.

The electron transport material provided in the embodiments of the application introduces electron withdrawing groups, the material has a relatively deep HOMO energy level and LUMO energy level, and a large-conjugated plane configuration in a molecule is conducive to an electron flow of the electron transport material. Therefore, the electron mobility of the material is improved, and the balance of electron transport and hole transport when it is applied to the organic light-emitting diode can be ensured, the display effect of the device is enhanced, and the luminous efficiency of the device is improved.

DESCRIPTION OF SPECIFIC EMBODIMENTS OF THE INVENTION

Technical solutions in embodiments of the present application will be clearly and completely described below in conjunction with the drawings in the embodiments of the present application. Obviously, the described embodiments are only a part of the embodiments of the present application, rather than all the embodiments. Based on the embodiments in this application, all other embodiments obtained by those skilled in the art without creative work shall fall within the protection scope of this application.

The embodiments of the present application provide an electron transport material and a fabricating method thereof, and an organic light-emitting diode. Detailed descriptions are given below. It is noted that an order of description in the following embodiments is not meant to limit the preferred order of the embodiments. In addition, in the description of this application, the term "including" means "including but not limited to". The terms first, second, etc. are only used as indicated, and do not impose numerical requirements or establish a sequence. Various embodiments of the present disclosure may exist in a range of forms. It should be understood that the description in a range format is only for convenience and brevity, and should not be construed as a rigid limit to the scope of the present disclosure. Therefore, it should be considered that the stated range description has specifically disclosed all possible subranges as well as a single value within that range. For example, it should be considered that the description of the range from 0.8 to 1.2 has specifically disclosed sub-ranges, such as from 0.8 to 0.9, from 0.9 to 1.1, from 0.9 to 1.2, etc., and a single number within the range, such as 0.8, 0.9, 1, or 1.2. This applies regardless of the scope. In addition, whenever a numerical range is indicated herein, it is meant to include any quoted number (fraction or integer) within the indicated range.

An embodiment of the present application provides an electron transport material having a structural formula shown in formula (I):

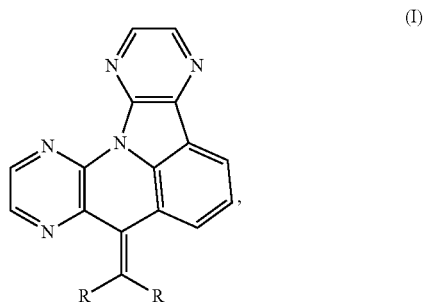

(I)

wherein, each time R appears, each R is independently selected from one or more of a C6-C60 substituted aryl group, a C6-C60 unsubstituted aryl group, or a C3-C60 heteroaryl group. That is, each R is independently selected from a C6-C60 substituted, a C6-C60 unsubstituted aryl group, or a C3-C60 heteroaryl group, and the selected R may be the same or different.

In the present disclosure, the term "aryl" refers to a group having 6-60 carbon atoms in its molecular structure and containing at least one aromatic ring. The aryl group can be an independent aryl group (unsubstituted aryl) or a combination group of aryl and other groups (substituted aryl). For example, a combined group of an aryl group and a cyano group. The term "heteroaryl" refers to an aromatic heterocyclic ring having at least one ring heteroatom (such as nitrogen, oxygen, and sulfur). Heteroaryl groups include monocyclic ring systems and polycyclic ring systems.

Further, the unsubstituted aryl group comprises:

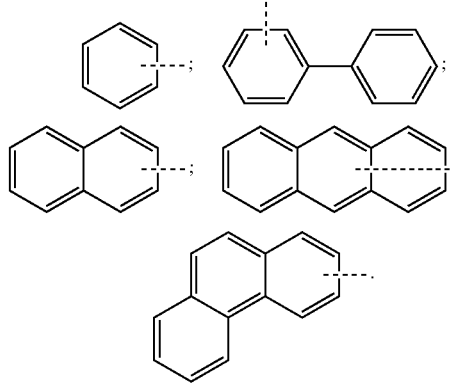

The substituted aryl group comprises:

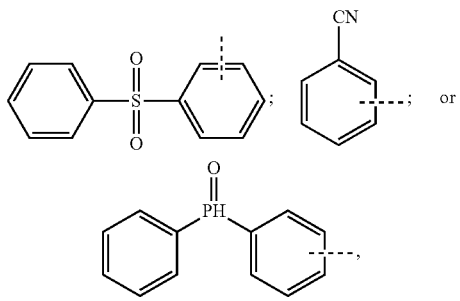

where a dotted line indicates a connection site, and P in the group represents a phosphorus atom.

The heteroaryl group comprises:

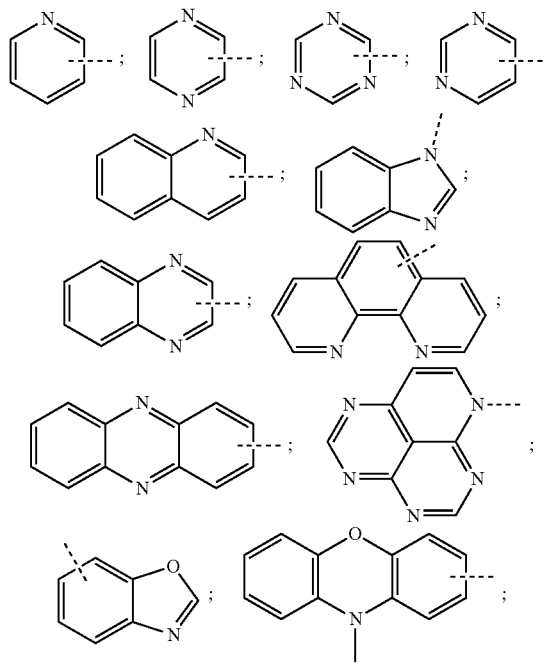

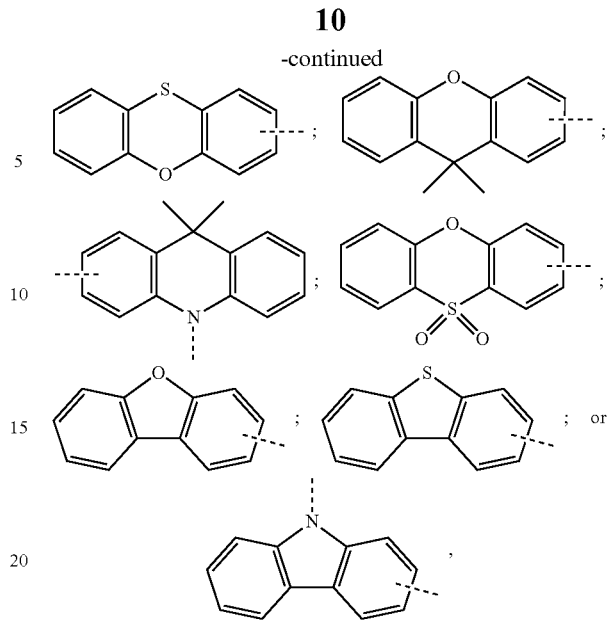

wherein a dotted line indicates a connection site, and two dotted lines appearing in a group indicate that any position of the dotted line can be used as a connection site, but only one of the connection sites is connected when connecting.

From above, the groups referred to by "C6-C60 substituted aryl group, C6-C60 unsubstituted aryl groups, or C3-C60 heteroaryl groups" include the above groups, and each R can be independently selected from these groups.

An embodiment of the present application also provides a method of fabricating the above-mentioned electron transport material, which includes following steps of:

fabricating the electron transport material based on a McMurray reaction of a first compound and a second compound, wherein: a structural formula of the first compound is as formula (II):

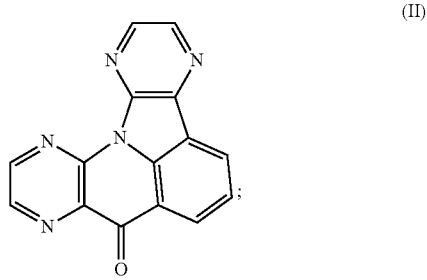 [SMILES: O=c1c2cccc3c4nccnc4n(c4nccnc14)c23]

(II)

a structural formula of the second compound is as formula (III):

(III)

wherein, each time R1 appears, each R1 is independently selected from one or more of a C6-C60 substituted aryl group, a C6-C60 unsubstituted aryl group, or a C3-C60 heteroaryl group. A molar ratio of the first compound to the second compound is 0.8~1.2:0.8~1.2, and an appropriate molar ratio can ensure sufficient reaction. The second compound can be selected from benzophenone, 4,4'-diphenylbenzophenone, etc.

Further, the step of fabricating the electron transport material based on the McMurray reaction of the first compound and the second compound comprises steps of:
providing a reaction solvent and a catalyst for the McMurray reaction; and
reacting the first compound and the second compound under conditions of the reaction solvent and the catalyst until conversion rates of the first compound and the second compound are both above 95%; and
extracting an organic matter after quenching.

The reaction solvent and catalyst are used to construct reaction conditions. The reaction solvent and the catalyst can be mixed first, and then the reactants (first compound, second compound) can be mixed, or the reactants, reaction solvent, and catalyst can be mixed at the same time. The conversion rate of the reactants can be monitored by high performance liquid chromatography (high performance liquid chromatography, HPLC), thin-layer chromatography (TLC) can also be used to monitor the progress of the reaction, and the reaction can even be measured by the reaction time.

Specifically, the step of reacting the first compound and the second compound under conditions of the reaction solvent and the catalyst comprises:
a preliminary step of: mixing and reacting the reaction solvent with the catalyst to obtain a mixture; and
a reaction step of: mixing the organic solvent with the mixture, and heating to reflux, wherein the first compound and the second compound are dissolved in the organic solvent.

The catalyst includes a first catalyst and a second catalyst. Zinc powder (metal powder) is selected as the first catalyst. Titanium tetrachloride (titanium chloride) is selected as the second catalyst. Tetrahydrofuran is selected as the reaction solvent. A molar ratio of tetrahydrofuran, zinc powder, and titanium tetrachloride is 35~45:1.5~2.5:0.8~1.2. The reaction conditions constructed by tetrahydrofuran, zinc powder, and titanium tetrachloride can provide a good reaction basis for the reaction between the first compound and the second compound, and an appropriate substance ratio can effectively promote the reaction between the first compound and the second compound. Of course, other catalysts and reaction solvents suitable for McMurray reactions can also be selected. There are many choices of compounds involved in the reaction conditions, which will not be repeated here.

In the preliminary step, the step of mixing the reaction solvent and the catalyst may include: mixing tetrahydrofuran with zinc powder under protective gas conditions, then mixing with titanium tetrachloride, and heating and refluxing for 2 to 3 hours. The atmosphere of the protective gas is selected to avoid the generation of impurities, and the protective gas can be selected from one or more of inert gas or nitrogen. The mixing of tetrahydrofuran, zinc powder, and titanium tetrachloride can keep the temperature of the resulting mixture at −10~10° C. In this way, the contact exotherm between the substances can be effectively alleviated, thereby ensuring the construction of the preliminary conditions for the reaction between the first compound and the second compound. The equipment used for mixing can be a laboratory container (such as a three-necked round bottom flask, an Erlenmeyer flask), or an industrial mixing equipment (such as an industrial mixer, a material mixer). After tetrahydrofuran and zinc powder are thoroughly mixed, titanium tetrachloride can be slowly added dropwise to the mixture formed by zinc powder and tetrahydrofuran using a syringe. The slow dropwise addition operation mode can also slow down the exotherm. After the tetrahydrofuran, zinc powder, and titanium tetrachloride are mixed, the material obtained by mixing tetrahydrofuran, zinc powder, and titanium tetrachloride can also be heated to room temperature and stirred for 0.3 to 0.7 h before heating to reflux for 2~3 h to mix evenly and to fully react.

In the reaction step, the molar ratio of the first compound, the second compound, and the organic solvent is 0.8~1.2:0.8~1.2:9~10. Tetrahydrofuran can be selected as the organic solvent. The organic solvent in which the first compound and the second compound are dissolved can be slowly added dropwise to the mixture obtained in the preliminary step, and then heated to reflux until the conversion rates of the first compound and the second compound are both above 95%, such that the carbonyl compounds are fully consumed—the process takes about 10-17 h.

The step of quenching after reacting the first compound and the second compound under conditions of the reaction solvent and the catalyst comprises: quenching with a carbonate solution after a substance obtained by the reaction is cooled to room temperature, so as to reduce or even avoid the formation of by-products. A mass concentration of the carbonate solution is 8-12%, and the carbonate is selected from one or more of potassium carbonate or sodium carbonate.

After quenching, when extracting an organic matter, it can be extracted by distillation or by using an extractant. Common extractants that can extract organic matter can be used, such as dichloromethane and toluene.

After the organic matter is extracted, the method may comprise the following step of: concentrating the organic matter, and purifying the obtained crude matter by flash chromatography. Through the operation of the subsequent steps, the purity of the target substance can be improved, thereby establishing a good foundation for the subsequent application of the electron transport material.

In addition, an embodiment of the present application also provides an organic light-emitting diode, which includes an electron transport layer, and the electron transport layer includes the above-mentioned electron transport material. The organic light-emitting diode also includes a cathode, an anode, a light-emitting layer, and a hole transport layer. Of course, it may also include other functional layers such as a hole injection layer/blocking layer. The cathode material can be silver (Ag), aluminum (Al), gold (Au), and other commonly used cathode materials in this field. The anode material can be indium tin oxide (ITO), fluorine-doped tin oxide (FTO), and other commonly used anode materials in this field. The light-emitting layer material can be Almq3, TBADN, CdSe, GaN, InN, and other commonly used light-emitting layer materials in this field. A material of the hole transport layer can be poly(9,9-dioctylfluorene-co-n-(4-butylphenyl)diphenylamine) (TFB), polyvinylcarbazole (PVK), polytriphenylamine (Poly-TPD), tris(4-(9carbazolyl)phenyl)amine (TCTA), 4,4'-N,N'-dicarbazole biphenyl (CBP), and other commonly used hole transport layer materials in this field.

According to a direction of emitting light, the organic light-emitting diode provided in the present application can be made into any one of a top emitter device, a bottom emitter device, and a double-sided emitting device. According to the division of the substrate, the organic light-emitting diode provided in the present application can be made into a device with a rigid glass substrate as a substrate, or a device with a flexible substrate as a substrate.

Embodiment 1

The present embodiment provides a method of fabricating an electron transport material M1, which includes following steps:

Under Ar atmosphere, 1.6 g (24 mmol) of zinc powder and 40 mL of tetrahydrofuran are added to a three-necked round-bottom flask equipped with a magnetic stirrer, and the temperature of the substance in the three-necked round-bottom flask is kept at −5° C. Then, 1.3 mL (12 mmol) TiCl₄ is slowly dropped into the three-necked round bottom flask through a syringe, and the temperature of the obtained substance is kept at −10~0° C. The obtained substance is heated to room temperature and is stirred for 0.5 h, and then is heated to reflux for 2.5 h, so as to obtain a first mixture.

5.46 g (20 mmol) of the first compound (A) and 3.65 g (20 mmol) of the second compound (B) are dissolved in 15 mL of tetrahydrofuran. Then, the obtained substance is slowly added dropwise to the suspended first mixture. After the addition is complete, the suspended first mixture is heated to reflux for 14 hours until the carbonyl compound is consumed (monitored by TLC), and a second mixture is obtained.

After the second mixture is cooled to room temperature, the reaction is quenched with a K₂CO₃ solution with a mass concentration of 10%, and the organic matter is extracted with CH₂Cl₂, and then being concentrated. A crude matter is purified by flash chromatography to obtain the target product M1.

The present embodiment also provides the electron transport material M1 fabricated by the above-mentioned preparation method, which has a synthesis route referring to:

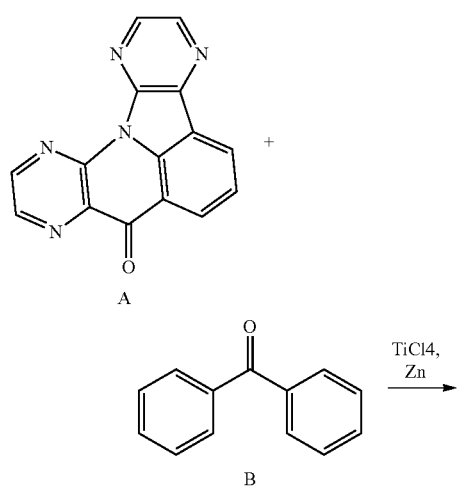

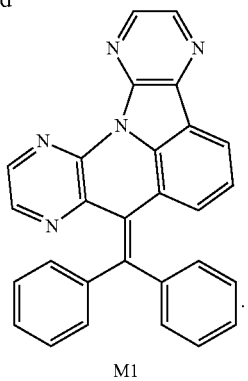

The embodiment also provides an organic light-emitting diode (device 1) to which the electron transport material M1 is applied. The organic light-emitting diode comprises: an anode, a hole injection layer, a hole transport layer, a light-emitting layer, an electron transport layer, a cathode stacked on a glass substrate, and a capping layer (CPL) stacked on a side of the cathode away from the electron transport layer, so as to jointly form a ITO/HAT-CN/TAPC/DPVBi/M1/Mg:Ag/HT structure.

Embodiment 2

The present embodiment provides a method of fabricating an electron transport material M2, which includes following steps:

Under Ar atmosphere, 1.6 g (24 mmol) of zinc powder and 40 mL of tetrahydrofuran are added to a three-necked round-bottom flask equipped with a magnetic stirrer, and the temperature of the substance in the three-necked round-bottom flask is kept at −5° C. Then, 1.3 mL (12 mmol) TiCl₄ is slowly dropped into the three-necked round bottom flask through a syringe, and the temperature of the obtained substance is kept at −10~0° C. The obtained substance is heated to room temperature and is stirred for 0.5 h, and then is heated to reflux for 2.5 h, so as to obtain a first mixture.

5.46 g (20 mmol) of the first compound (A) and 6.68 g (20 mmol) of the second compound (B) are dissolved in 15 mL of tetrahydrofuran. Then, the obtained substance is slowly added dropwise to the suspended first mixture. After the addition is complete, the suspended first mixture is heated to reflux for 14 hours until the carbonyl compound is consumed (monitored by TLC), and a second mixture is obtained.

After the second mixture is cooled to room temperature, the reaction is quenched with a K₂CO₃ solution with a mass concentration of 10%, and the organic matter is extracted with CH₂Cl₂, and then being concentrated. A crude matter is purified by flash chromatography to obtain the target product M2.

The present embodiment also provides the electron transport material M2 fabricated by the above-mentioned preparation method, which has a synthesis route referring to:

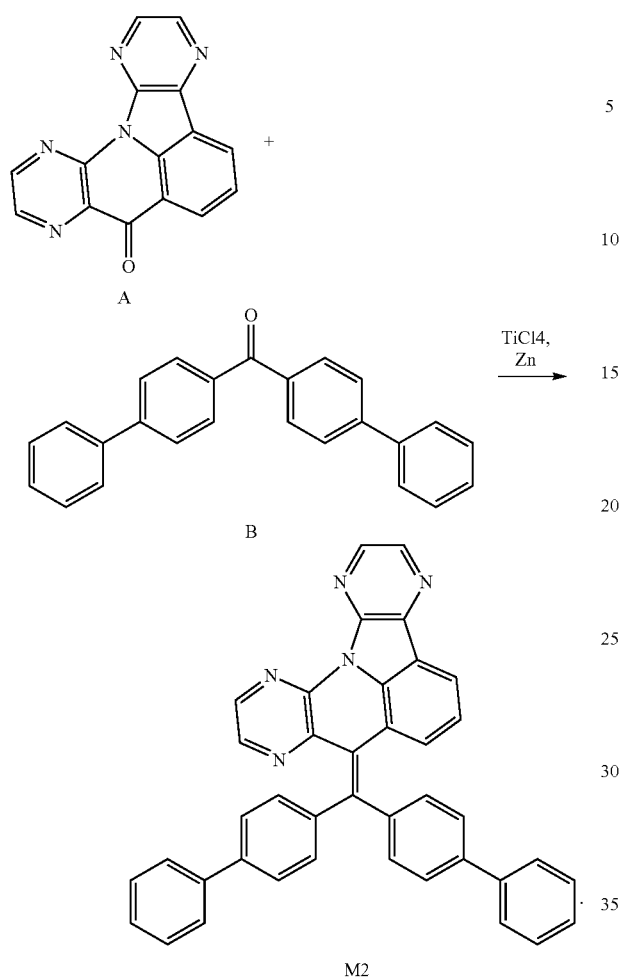

M2

The embodiment also provides an organic light-emitting diode (device 2) to which the electron transport material M2 is applied. The organic light-emitting diode comprises: an anode, a hole injection layer, a hole transport layer, a light-emitting layer, an electron transport layer, a cathode stacked on a glass substrate, and a capping layer stacked on a side of the cathode away from the electron transport layer, so as to jointly form a ITO/HAT-CN/TAPC/DPVBi/M2/Mg:Ag/HT structure.

Embodiment 3

The present embodiment provides a method of fabricating an electron transport material M3, which includes following steps:

Under Ar atmosphere, 1.6 g (24 mmol) of zinc powder and 40 mL of tetrahydrofuran are added to a three-necked round-bottom flask equipped with a magnetic stirrer, and the temperature of the substance in the three-necked round-bottom flask is kept at −5° C. Then, 1.3 mL (12 mmol) TiCl$_4$ is slowly dropped into the three-necked round bottom flask through a syringe, and the temperature of the obtained substance is kept at −10~0° C. The obtained substance is heated to room temperature and is stirred for 0.5 h, and then is heated to reflux for 2.5 h, so as to obtain a first mixture.

5.46 g (20 mmol) of the first compound (A) and 5.64 g (20 mmol) of the second compound (B) are dissolved in 15 mL of tetrahydrofuran. Then, the obtained substance is slowly added dropwise to the suspended first mixture. After the addition is complete, the suspended first mixture is heated to reflux for 14 hours until the carbonyl compound is consumed (monitored by TLC), and a second mixture is obtained.

After the second mixture is cooled to room temperature, the reaction is quenched with a K$_2$CO$_3$ solution with a mass concentration of 10%, and the organic matter is extracted with CH$_2$Cl$_2$, and then being concentrated. A crude matter is purified by flash chromatography to obtain the target product M3.

The present embodiment also provides the electron transport material M3 fabricated by the above-mentioned preparation method, which has a synthesis route referring to:

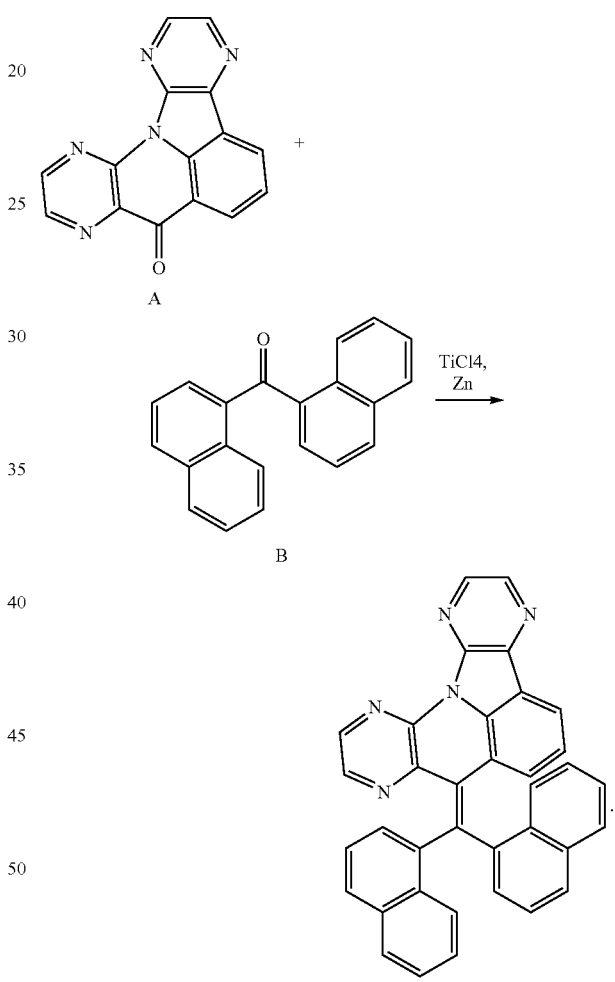

M3

The embodiment also provides an organic light-emitting diode (device 3) to which the electron transport material M3 is applied. The organic light-emitting diode comprises: an anode, a hole injection layer, a hole transport layer, a light-emitting layer, an electron transport layer, a cathode stacked on a glass substrate, and a capping layer stacked on a side of the cathode away from the electron transport layer, so as to jointly form a ITO/HAT-CN/TAPC/DPVBi/M3/Mg:Ag/HT structure.

Embodiment 4

The present embodiment provides a method of fabricating an electron transport material M4, which includes following steps:

At a temperature of −2° C. and a nitrogen atmosphere, 16 mmol of zinc powder and 430 mmol of tetrahydrofuran are added to a three-necked round bottom flask equipped with a magnetic stirrer. Then, 10 mmol of $TiCl_4$ is slowly dropped into the three-necked round bottom flask through a syringe. The obtained substance is heated to room temperature and stirred for 0.7 h, and then is heated to reflux for 2 h, so as to obtain the first mixture.

16 mmol of the first compound (A) and 20 mmol of the second compound (B) are dissolved in 180 mmol of tetrahydrofuran. Then, the obtained substance is slowly added dropwise to the suspended first mixture. After the addition is complete, the suspended first mixture is heated to reflux until the conversion rate of the first compound and the second compound reaches 95% (monitored by HPLC), and a second mixture is obtained.

After the second mixture is cooled to room temperature, the reaction is quenched with a $Na_2CO_3$ solution with a mass concentration of 9%, and the organic matter is extracted with toluene and then being concentrated. A crude matter is purified by flash chromatography to obtain the target product M4.

This embodiment also provides the electron transport material M4 fabricated by the above fabricating method and the organic light-emitting diode using M4. The organic light-emitting diode includes an anode, a hole transport layer, a light-emitting layer, an electron transport layer, and a cathode stacked on a glass substrate, so as to form an FTO/PVK/TBADN/M4/Ag structure.

Embodiment 5

The present embodiment provides a method of fabricating an electron transport material M5, which includes following steps:

At a temperature of 7° C. and a nitrogen atmosphere, 22 mmol of zinc powder and 350 mmol of tetrahydrofuran are added to a three-necked round bottom flask equipped with a magnetic stirrer. Then, 11 mmol of $TiCl_4$ is slowly dropped into the three-necked round bottom flask through a syringe. The obtained substance is heated to room temperature and stirred for 0.4 h, and then is heated to reflux for 3 h, so as to obtain the first mixture.

22 mmol of the first compound (A) and 18 mmol of the second compound (B) are dissolved in 190 mmol of tetrahydrofuran. Then, the obtained substance is slowly added dropwise to the suspended first mixture. After the addition is complete, the suspended first mixture is heated to reflux until the conversion rate of the first compound and the second compound reaches 95% (monitored by HPLC), and a second mixture is obtained.

After the second mixture is cooled to room temperature, the reaction is quenched with a $Na_2CO_3$ solution with a mass concentration of 10%, and the organic matter is extracted with dichloromethane and then being concentrated. A crude matter is purified by flash chromatography to obtain the target product M5.

This embodiment also provides the electron transport material M5 fabricated by the above fabricating method and the organic light-emitting diode using M5. The organic light-emitting diode includes an anode, a hole transport layer, a light-emitting layer, an electron transport layer, and a cathode laminated on a polyethylene terephthalate (PET) flexible substrate, so as to form an IZO/Poly-TPD/Almq3/M5/Ag structure.

Comparative Example

The organic light-emitting diode (device 4) of the comparative example includes: an anode, a hole injection layer, a hole transport layer, a light-emitting layer, an electron transport layer, and a cathode laminated on a glass substrate, and a capping layer stacked on a side of the cathode away from the electron transport layer to jointly form an ITO/HAT-CN/TAPC/DPVBi/BCP/Mg:Ag/HT structure.

In order to reflect the performance of the electronic transport materials prepared in the examples of this application, the electronic transport materials of Embodiments 1 to 3 are tested using software, etc. The energy level can be completed by Guassian 09 software. Molecular structure optimization can be done with a time-dependent density functional (TD-DFT) method "B3LYP" and a basis set "6-31g(d)". Results are shown in Table 1, where Eg represents a width of forbidden band.

TABLE 1

Electron transport material properties:

| Electron transport material | HOMO (eV) | LUMO (eV) | Eg (eV) |
|---|---|---|---|
| M1 | −5.26 | −1.98 | 3.28 |
| M2 | −5.16 | −2.06 | 3.10 |
| M3 | −5.26 | −2.00 | 3.26 |

The performance data of blue electroluminescent devices prepared using the electron transport materials of Embodiments 1 to 3 are shown in Table 2. E/CIEy is a parameter to measure blue light luminous efficiency. E represents current efficiency. CIEy represents the color coordinate (ordinate) of the light color of the device. LT95 represents the life decay time of the device, i.e., the time it takes for the luminous efficiency of the device to decay to 95%.

TABLE 2 device performances:

| Device | Electron transport material | Driving voltage (V) | E/CIEy | LT95 (h) |
|---|---|---|---|---|
| Device 1 | M1 | 3.79 | 147.5 | 75 |
| Device 2 | M2 | 3.83 | 149.9 | 79 |
| Device 3 | M3 | 3.81 | 152.1 | 77 |
| Device 4 | BCP | 3.83 | 138.7 | 71 |

It can be seen from Table 2 that the electroluminescent devices (devices 1 to 3) fabricated by the electron transport materials of Embodiments 1 to 3 have lower driving voltage, higher B.I. luminous efficiency, and longer device life.

The electron transport material and the fabricating method thereof, and the organic light-emitting diode provided by the embodiments of the present application are described in detail above. Specific examples are used in this article to illustrate the principles and implementation of the application, and the descriptions of the above examples are only used to help understand the methods and core ideas of the application. At the same time, for those skilled in the art, according to the idea of this application, there will be changes in the specific implementation and the scope of application. In summary, the content of this specification should not be construed as a limitation on this application.

The invention claimed is:

1. An electron transport material, wherein a molecular structure of the electron transport material has a structural formula shown in formula (I):

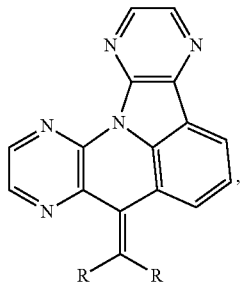

(I)

wherein, each time R appears, each R is independently selected from one or more of a C6-C60 substituted aryl group, a C6-C60 unsubstituted aryl group, or a C3-C60 heteroaryl group.

2. The electron transport material according to claim 1, wherein the unsubstituted aryl group comprises:

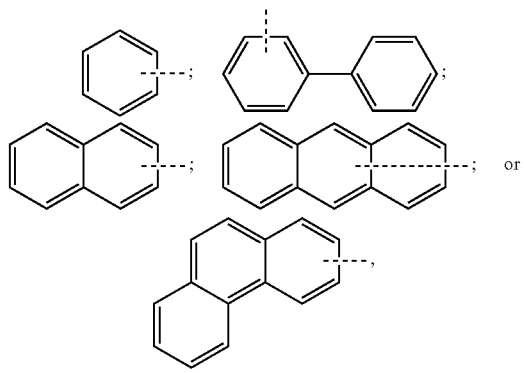

wherein a dotted line indicates a connection site.

3. The electron transport material according to claim 1, wherein the substituted aryl group comprises:

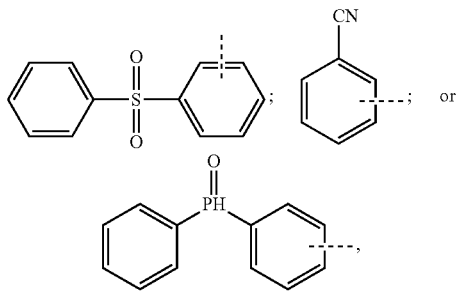

wherein a dotted line indicates a connection site.

4. The electron transport material according to claim 1, wherein the heteroaryl group comprises:

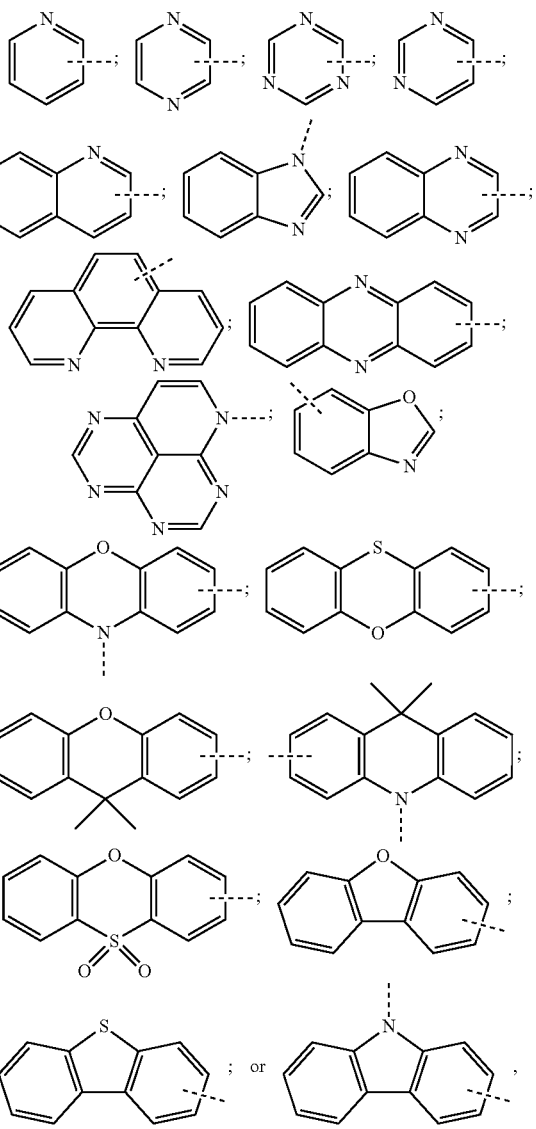

wherein a dotted line indicates a connection site.

5. A method of fabricating an electron transport material, comprising following steps of:

fabricating the electron transport material based on a McMurray reaction of a first compound and a second compound, wherein: a structural formula of the first compound is as formula (II):

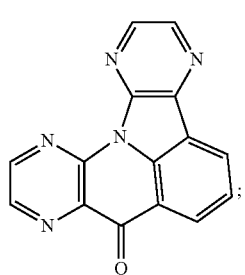

(II)

a structural formula of the second compound is as formula (III):

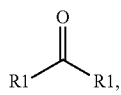
(III)

wherein, each time R1 appears, each R1 is independently selected from one or more of a C6-C60 substituted aryl group, a C6-C60 unsubstituted aryl group, or a C3-C60 heteroaryl group.

6. The method of fabricating the electron transport material according to claim 5, wherein a molar ratio of the first compound to the second compound is 0.8~1.2:0.8~1.2.

7. The method of fabricating the electron transport material according to claim 5, wherein the second compound is selected from one or more of:

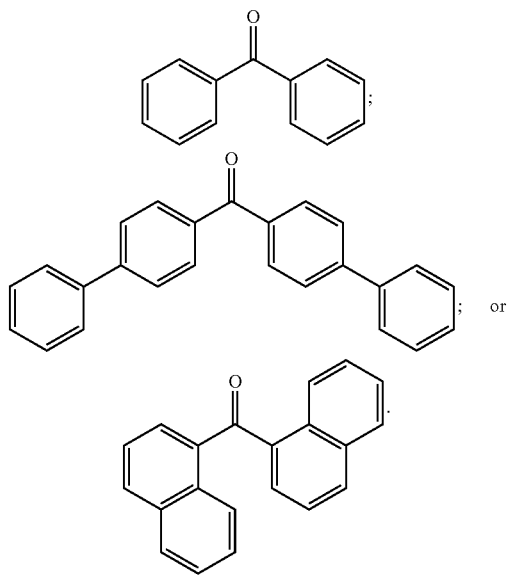

; or

8. The method of fabricating the electron transport material according to claim 5, wherein the step of fabricating the electron transport material based on the McMurray reaction of the first compound and the second compound comprises steps of:
providing a reaction solvent and a catalyst for the McMurray reaction; and
reacting the first compound and the second compound under conditions of the reaction solvent and the catalyst until conversion rates of the first compound and the second compound are both above 95%; and
extracting an organic matter after quenching.

9. The method of fabricating the electron transport material according to claim 8, wherein the step of reacting the first compound and the second compound under conditions of the reaction solvent and the catalyst comprises steps of:
mixing and reacting the reaction solvent with the catalyst to obtain a mixture; and
mixing the organic solvent with the mixture and heating to reflux, wherein the first compound and the second compound are dissolved in the organic solvent.

10. The method of fabricating the electron transport material according to claim 9, wherein a molar ratio of the first compound to the organic solvent is 0.8~1.2:9~10.

11. The method of fabricating the electron transport material according to claim 8, wherein the step of quenching comprises: quenching with a carbonate solution after a substance obtained by the reaction is cooled to room temperature.

12. The method of fabricating the electron transport material according to claim 11, wherein a mass concentration of the carbonate solution is 8-12%.

13. The method of fabricating the electron transport material according to claim 8, wherein the catalyst comprises a first catalyst and a second catalyst, and a molar ratio of the reaction solvent, the first catalyst, and the second catalyst is 35-45:1.5-2.5:0.8-1.2.

14. The method of fabricating the electron transport material according to claim 13, wherein the first catalyst is metal powder, and the second catalyst is titanium chloride.

15. The method of fabricating the electron transport material according to claim 8, wherein the conversion rates of the first compound and the second compound are monitored by high performance liquid chromatography.

16. An organic light-emitting diode, comprising an electron transport layer, wherein the electron transport layer comprises an electron transport material, and a molecular structure of the electron transport material has a structural formula shown in formula (I):

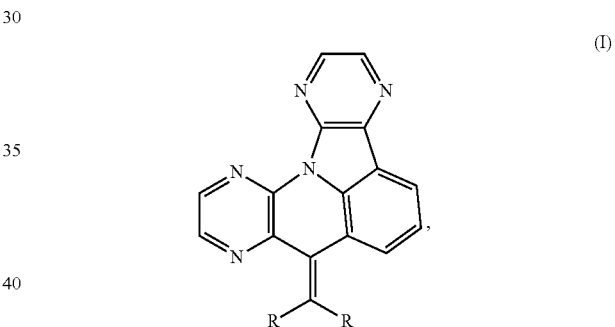
(I)

wherein, each time R appears, each R is independently selected from one or more of a C6-C60 substituted aryl group, a C6-C60 unsubstituted aryl group, or a C3-C60 heteroaryl group.

17. The organic light-emitting diode according to claim 16, wherein the unsubstituted aryl group comprises:

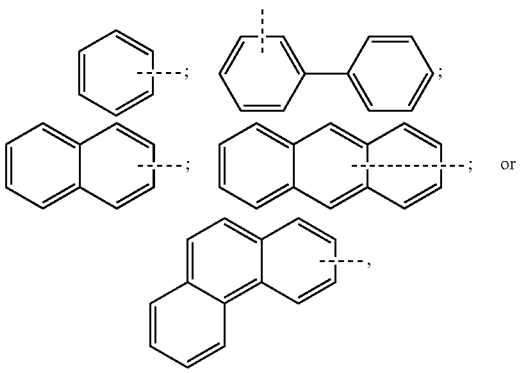

wherein a dotted line indicates a connection site.

18. The organic light-emitting diode according to claim 16, wherein the substituted aryl group comprises:

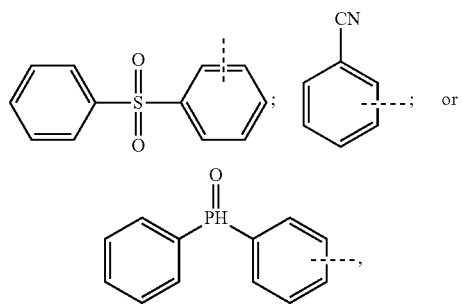

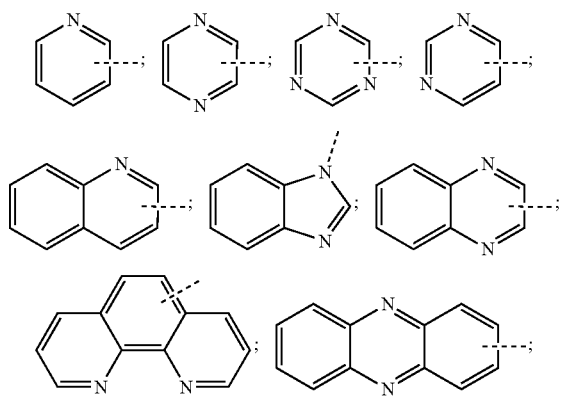

wherein a dotted line indicates a connection site.

19. The organic light-emitting diode according to claim 16, wherein the heteroaryl group comprises:

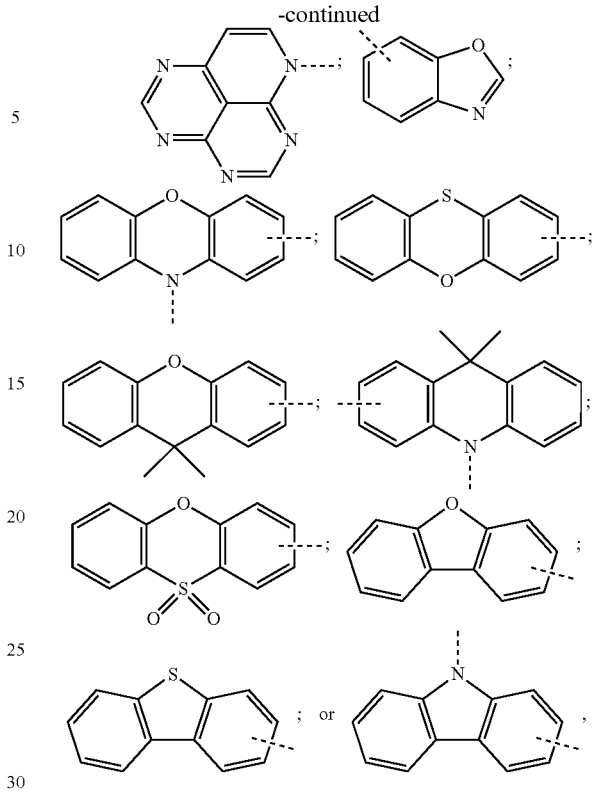

wherein a dotted line indicates a connection site.

20. The organic light-emitting diode according to claim 16, wherein the organic light-emitting diode further comprises: a cathode, a light-emitting layer, a hole transport layer, and an anode, wherein the anode, the hole transport layer, the light-emitting layer, the electron transport layer, and the cathode are laminated.

* * * * *